US006461700B2

(12) United States Patent
Paschke et al.

(10) Patent No.: US 6,461,700 B2
(45) Date of Patent: Oct. 8, 2002

(54) AROMATIC ACID MONOMERS, POLYMERS, PRODUCTS AND PROCESSES FOR THEIR MANUFACTURE

(75) Inventors: Edward E. Paschke, Wheaton, IL (US); Bruce I. Rosen, Morton Grove, IL (US); David A. Peterson, Westmont, IL (US); David E. James, Batavia, IL (US); Melvin L. Luetkens, Jr., Batavia, IL (US); Charles W Bauer, Batavia, IL (US); Gary T. Brooks, Naperville, IL (US)

(73) Assignee: BP Corporation North America Inc., Chicago, IL (US)

( * ) Notice: Subject to any disclaimer, the term of this patent is extended or adjusted under 35 U.S.C. 154(b) by 0 days.

(21) Appl. No.: 09/935,458

(22) Filed: Aug. 23, 2001

(65) Prior Publication Data

US 2002/0016499 A1 Feb. 7, 2002

Related U.S. Application Data

(62) Division of application No. 09/412,458, filed on Oct. 4, 1999, now Pat. No. 6,284,920.
(60) Provisional application No. 60/138,344, filed on Jun. 9, 1999, and provisional application No. 60/103,393, filed on Oct. 7, 1998.

(51) Int. Cl.$^7$ .......................... B29D 22/00; C08G 63/02
(52) U.S. Cl. ...................... 428/35.7; 562/483; 562/485; 562/486; 562/487; 562/488; 528/298; 528/302; 528/308; 528/308.6; 428/357; 428/364
(58) Field of Search ................................. 562/483, 485, 562/486, 487, 488; 528/298, 302, 308, 308.6; 428/35.7, 357, 364

(56) References Cited

U.S. PATENT DOCUMENTS

| | | | | | |
|---|---|---|---|---|---|
| 4,719,311 A | * | 1/1988 | Partenheimer | ............... | 562/413 |
| 4,933,491 A | * | 6/1990 | Albertins et al. | ............ | 562/416 |
| 4,950,786 A | * | 8/1990 | Sanchez et al. | ............. | 502/304 |
| 5,041,633 A | * | 8/1991 | Partenheimer et al. | ....... | 562/413 |
| 5,159,109 A | * | 10/1992 | Rosen et al. | ................. | 562/486 |
| 5,183,933 A | * | 2/1993 | Harper et al. | .................. | 502/28 |
| 5,256,817 A | * | 10/1993 | Sikkenga et al. | ............ | 562/416 |
| 5,262,560 A | * | 11/1993 | Holzhauer et al. | ........... | 560/100 |
| 5,292,934 A | * | 3/1994 | Sikkenga et al. | ............ | 562/413 |
| 5,563,294 A | * | 10/1996 | Holzhauer et al. | .......... | 562/483 |
| 5,629,446 A | * | 5/1997 | Holzhauer et al. | .......... | 562/298 |
| 5,728,870 A | * | 3/1998 | Holzhauer et al. | .......... | 562/483 |
| 5,770,764 A | * | 6/1998 | Zeitlin et al. | ................ | 562/412 |

* cited by examiner

*Primary Examiner*—Samuel A. Acquah
(74) *Attorney, Agent, or Firm*—Anthony R. Chi

(57) ABSTRACT

Processes for producing aromatic monomers useful for forming polyesters are disclosed. Cost effective steps employed in the processes permit small amounts of process-related materials typically removed from monomer to remain in an aromatic monomer product. In many cases, the presence of the process-related materials left in the monomer product by the cost effective process steps can enhance the performance of the monomer in certain applications. Aromatic monomer products and polymers produced therefrom having these advantages also are disclosed, as well as products such as pasteurizable bottles made from these polymers

16 Claims, No Drawings

AROMATIC ACID MONOMERS, POLYMERS, PRODUCTS AND PROCESSES FOR THEIR MANUFACTURE

RELATED APPLICATIONS

This is a division of application Ser. No. 09/412,458 filed Oct. 4, 1999, now U.S. Pat. No. 6,284,920.

This application claims the benefit of U.S. Provisional Patent Application No. 60/138,344, entitled "Aromatic Acid Monomers, Polymers, Products and Processes for Their Manufacture", filed Jun. 9, 1999, and U.S. Provisional Patent Application No. 60/103,393, entitled "Aromatic Acid Monomers, Polymers, Products and Processes for Their Manufacture", filed Oct. 7, 1998.

FIELD OF THE INVENTION

The invention generally relates to polymers formed from aromatic acids. More particularly, the invention relates to aromatic acid monomers which contain small amounts of materials that can provide unexpected advantages during the polymerization or copolymerization of those acid monomers, as well as to processes for manufacturing such aromatic acid monomers and polymers.

BACKGROUND OF THE INVENTION

The manufacture of aromatic acids useful as monomers typically is a complex, multistep process. For example, 2,6-naphthalenedicarboxylic acid (2,6-NDA) can be manufactured by a five step synthesis process which includes the steps of reacting o-xylene and butadiene in an alkenylation reaction to produce 5-ortho-tolylpentene, cyclizing the 5-ortho-tolylpentene to form 1,5-dimethyltetralin (1,5-DMT), dehydrogenating the 1,5-DMT to produce 1,5-dimethylnaphthalene (1,5-DMN), isomerizing the 1,5-DMN to produce 2,6-dimethylnaphthalene (2,6-DMN), and oxidizing the 2,6-DMN to produce 2,6-NDA.

Crude NDA produced by such a process will contain a wide variety of what are believed to be undesired process-related materials. Many of these materials will be isomers of 2,6-NDA or mono- or trifunctional reaction products. Other undesired process-related materials contained in the crude NDA will be reagents such as catalyst metals carried through the various reactions steps, and color bodies formed during the reaction steps. As used herein, the term "process-related material" means any material that is formed or added in any process step leading up to the manufacture of aromatic acid monomer product, including but not limited to, catalysts, products of side reactions, undesired oxidation products, undesired isomers and the like.

It is believed that in the preparation of polyesters from monomers such as NDA, monomer purity is critical to satisfactorily achieving high molecular weight polymers and a sufficiently fast kinetic rate of polymerization. For this reason, polymer manufacturers typically require that monomer impurities such as mono-functional and tri-functional glycols and carboxylic acids be minimized or eliminated from monomers to be used in polymerization reactions. For example, terephthalic acid and isophthalic acid typically are expected to contain less than 200 parts per million or less by weight total of monocarboxylic and tricarboxylic acids. Similarly, ethylene glycol used in polymerization reactions typically is expected to contain no detectable impurities.

Tricarboxylic acids are thought to be undesirable because such trifunctional compounds can cause undesired cross-linking of polymer chains. Such cross-linking is reported to contribute to slow rates of crystallization and polymer brittleness, both of which are undesired characteristics in many applications. Additionally, when cross-linking becomes substantial, a "gel point" is reached. At this point, the polymer cannot be melt polymerized or melt fabricated and is no longer considered to be a thermoplastic material.

Monocarboxylic acids and other monofunctional materials are believed to be undesirable components in monomers because they act as "chain-stoppers" which inhibit the development of molecular weight and because they decrease reaction kinetics. If the concentration of such materials is too high, the polymerization rate can become zero due to termination of otherwise reactive end-groups.

Color bodies of various types are thought to be undesirable in monomers. The presence of color bodies in monomer can result in substantially greater color in a polymer than would appear likely from seemingly small amounts of color visible in a monomer, thus making even minute amounts of color bodies in monomers undesirable. As used herein, the term "color bodies" refers to any carboxylic acid containing process-related material present in a monomer or polymer that can contribute to the presence of color in the monomer or polymer if present in sufficient amount.

Metals such as entrained catalyst metals also are thought to be undesirable components in monomers. For example, entrained cobalt and manganese oxidation catalyst are believed to be undesirable monomer impurities because it is expected that they may affect the rate of polymerization and polymer color in an unpredictable way. Such metals also are thought to sometimes affect the amount of color visible in a monomer or polymer.

Because it is believed that the presence in monomer of undesired process-related materials such as byproducts, reagents and impurities like color bodies can result in an inferior polymer product, substantial effort typically is devoted to improving the purity of monomers such as 2,6 NDA to provide a quality of product deemed acceptable by customers.

For example, purified aromatic acids have been produced from crude aromatic acids by slurrying the effluent from a crude aromatic acid oxidation process, passing the slurry through a plurality of heaters until the reaction products are dissolved, passing the resulting solution over a purification catalyst, and thereafter crystallizing a purified product. Such a process requires substantial time and energy beyond that expended to produce crude aromatic acid, and therefore substantially increases the cost of the monomer.

Alternatively, high purity monomer can be manufactured by starting with a relatively high purity feedstock, such as a process in which relatively pure 2,6-naphthalenedicarboxylate (2,6-NDC) is hydrolyzed to form relatively pure NDA. This process also is cost intensive because of the complexity and expense of producing the relatively pure NDC feedstock.

What is needed is a cost effective way to produce aromatic acids such as NDA which are suitable for use in polymer applications.

SUMMARY OF THE INVENTION

Surprisingly, we have found that the presence of certain levels of process-related materials in aromatic acid monomers can result in monomers that perform as well as or better than higher purity aromatic acid monomers when used in many polymer applications.

In some applications, the presence of certain levels of catalyst metals can result in more rapid polycondensation and solid state polymerization reactions, thereby improving the economics of these polymerization reactions without affecting the desired properties of the polymer product.

In other applications, the presence of certain trifunctional materials in the aromatic acid monomer product provide for branching of polymer chains, thereby providing increased melt strength which is useful when molding articles from the polymer.

In still other applications, the presence of certain levels of metallic impurities and color bodies provides for an aromatic acid monomer that has a brownish cast that is useful in particular end uses, including but not limited to the packaging of drinks such as beer in brown polymer bottles.

While in some cases the foregoing aromatic acid monomers might be produced directly as solids separated from the product of an oxidation reaction, typically aromatic monomer product in accordance with the present invention will be produced by relatively simple post-processing of oxidized aromatic feedstocks, such as by slurrying or washing crude aromatic acid in an appropriate solvent under the appropriate process conditions. Monomer product manufactured in this way can be both less expensive and advantageous in certain end uses.

DETAILED DESCRIPTION OF THE INVENTION

The following detailed description of preferred embodiments of our invention focuses on the advantages of our invention with respect to the preparation of 2,6 naphthalenedicarboxylic acid monomer product and polymers made therefrom. As will be discussed later in more detail, the advantages of the invention also are believed to be useful in connection with other aromatic acid monomers such as terephthalic acid, isophthalic acid and other isomers of naphthalenedicarboxylic acids.

As noted above, 2,6-naphthalenedicarboxylic acid (2,6-NDA) can be manufactured by a five step synthesis process which includes the steps of reacting o-xylene and butadiene in an alkenylation reaction to produce 5-ortho-tolylpentene, cyclizing the 5-ortho-tolylpentene to form 1,5-dimethyltetralin (1,5-DMT), dehydrogenating the 1,5-DMT to produce 1,5-dimethyinaphthalene (1,5-DMN), isomerizing the 1,5-DMN to produce 2,6-dimethylnaphthalene (2,6-DMN), and oxidizing the 2,6-DMN to produce 2,6-NDA. Aromatic feedstocks such as the 2,6-DMN oxidized in this process preferably contain at least 97 mole percent of the feed material which is to be oxidized to the acid, calculated as a mole percent of all aromatic material in the feedstock.

Crude 2,6-NDA produced by the foregoing process preferably contains at least 93 mole percent acid monomer and typically is expected to contain unacceptable levels of one or more of the following materials: trifunctional materials, 1-bromo-2,6-NDA, 2-naphthoic acid, 6-formyl-2-naphthoic acid, cobalt, manganese, bromine, iron and various color bodies. We have found that it frequently is not harmful, and in many cases it is advantageous, to permit certain levels of metals, tri-functional compounds, and color bodies to be present in 2,6-NDA monomer product used in polymerization reactions. In many cases, these acceptable and advantageous material levels can be obtained by relatively simple processing of the oxidation product of 2,6-DMN, thereby eliminating the need for costly purification steps such as recrystallization.

Acceptable and preferred levels of the foregoing materials consistent with our invention are listed in Table 1, below. The ppm ranges listed refer to ppm by weight of the material present in NDA monomer product.

TABLE 1

| Material | Acceptable level | Preferred Level |
| --- | --- | --- |
| trifunctionals | 50 to 10,000 | 150 to 8,500 |
| monofunctionals | 50 to 5,000 | 150 to 3,500 |
| metals (Co + Mn) | 50 to 10,000 | 500 to 2,000 |
| color bodies | 50 to 500 | 50 to 250 |

NDA monomer having one or more of the foregoing materials in concentrations in accordance with our invention readily can be produced, for example, by slurrying crude NDA oxidation product to remove a fraction of such materials, while permitting a desirable, or at least non-deleterious, portion of such materials to remain in the monomer. As used herein, the term "slurry" refers to any process which employs a solvent to wash or disperse a crude oxidation product, but specifically excludes any process which dissolves greater than about 10 mole percent of a desired aromatic monomer present in crude oxidation product, such as a recrystallization step. Other examples of "slurry" processes in accordance with the invention include the use of higher solvent volumes in the reactor in which the aromatic feedstock is oxidized to render the process-related materials more soluble, thereby somewhat reducing the levels present in the product, adding or increasing the volume of solvent in the crystallizer train of the oxidation process to reduce the presence of process-related material by dilution, and the use of filtration with a solvent wash to reduce the level of process-related materials remaining in the monomer product.

For example, crude 2,6-naphthalenedicarboxylic acid can be recovered directly from 2,6-DMN oxidation mother liquor. The crude 2,6-NDA then can be redispersed or reslurried in a suitable solvent such as water, a low molecular weight carboxylic acid, or a mixture of water and a low molecular weight carboxylic acid at a weight ratio of about 0.1 to about 1 part of 2,6-naphthalene dicarboxylic acid per part of solvent. Preferred process conditions for the reslurry process include temperatures of from 60 to 125° C., with 75 to 110° C. being most preferred, and pressures of from about 0.5 to 3 atmospheres, with pressures from 1 to 2 atmospheres being most preferred. Solvent acid to water ratios can range from 100 percent acid to 100 percent water, with the preferred acid to water part ratio being from about to 90:10 to 50:50, with the most preferred ranges being about 80 parts acid and 20 parts water.

Preferably, at least a portion of the solvent used to redisperse or reslurry the 2,6-naphthalene dicarboxylic acid in this manner is a process stream or process-derived stream such as condensate from the overhead of the oxidation reaction mixture. In this case, solvent comprising water and an acid such as acetic acid can be returned, at least in part, to the oxidation reactor. Alternatively, the solvent can be distilled to recover the low molecular weight carboxylic acid for recycle to the oxidation reactor. Solvents may contain other process materials that will not substantially affect the slurry process or properties of the monomer product, such as alcohols or acetates generated in the process. Such process streams should, however, contain little or none of the process-related materials sought to be minimized in the slurry process.

The foregoing slurry step provides for a relatively purer 2,6-naphthalenedicarboxylic acid. In many cases, such a 2,6-NDA monomer product in accordance with the invention will be suitable or preferred for certain applications over a monomer product produced from a more complex process having additional purification steps.

After this slurry step, the 2,6-naphthalenedicarboxylic acid can be separated from the solvent by any method or methods known in the art for partitioning a solid from a liquid phase such as, for example, centrifugation, filtration, or settling.

Of particular interest in the reslurried NDA are the concentrations of catalyst metals such as cobalt and manganese, the ratio of cobalt and manganese metals, the level of multifunctional aromatic compounds, and the level of colored impurities.

The levels and ratios of catalytic metals are important both because they will affect the polymerization rate of the monomer and because their presence may, in some cases, influence the final polymer color. For NDA applications, the total amount of Co and Mn present in the reslurried material should be no more than about 10,000 ppm by weight in the reslurried product, with 500 to 2,000 ppm being preferred, and 1000 to 1,500 ppm being most preferred. The molar ratio of Co to Mn can range from 5:1 to 0.2:1, with the preferred ratios being between 4:1 to 0.25:1, and the most preferred ratios being between 3:1 and 0.5:1.

The levels of multifunctional materials are important when the polymer to be produced from the aromatic monomer requires additional melt strength. For NDA applications, trifunctional naphthalenic moieties are the more likely species, with 1,2,6-, 1,3,7- and 2,3,6- naphthalene tricarboxylic acids predominating in the mix. Preferably, these trifunctional species will be present in the reslurried NDA in an amount between 50 and about 10,000 ppm by weight, preferably between about 200 and 9,000 ppm by weight, and most preferably between about 150 and 8,500 ppm by weight. When other aromatic monomers such as PTA are the subject of the invention, trifunctional acids such as 1,2,3-, 1,2,4- and 1,3,5-benzene tricarboxylic acids, and mixtures thereof are the more likely trifunctional species, and may be present in the ranges set forth above for the napthalenic trifunctional species. Mixtures of any and all of the foregoing trifunctional impurities may, of course, be present in accordance with the invention, and impurities having a functionality greater than 3 may also be advantageously utilized in accordance with the invention. As used herein, the term "trifunctional material" means any process-related material having three functional groups capable of reacting with a glycol monomer under polymerization conditions. The term "multifunctional material" means any such material with a functionality of three or more.

Polyester color is a very important performance requirement in certain applications, while in other applications, color is not important. Sometimes, a color such as brown is required for certain packaging applications. The brown color typically is achieved by the addition of dyes which usually are high molecular weight organic compounds. Dyes are undesirable because they can detract from the polyester properties, especially barrier permeation to gases such as oxygen and carbon dioxide. Additionally, dyes are expensive, and can be undesirable from environmental and recycling standpoints. Thus, color bodies present in an aromatic acid monomer may be useful for inducing a color such as brown into subsequently formed polymers. Color bodies useful in accordance with the invention include benzcoumarin, pentaquinone, pentacene and flourenone structures containing carboxylic acid functions. Typically, these color bodies should be present in an amount between about 50 and about 500 ppm by weight, more preferably between about 50 and 250 ppm, and most preferably present at a level of about 150 ppm.

Slurried NDA in accordance with the invention also can contain monofunctional impurities including, but not limited to, such aromatic acid impurities as benzoic acid and benzoic acid substituted with groups such as methyl, bromo, and formyl groups, as well as 1- and 2-naphthoic acid and 1- and 2-naphthoic acid substituted with groups such as methyl, bromo, and formyl, and mixtures thereof. The concentration of monocarboxylic acids in a reslurried NDA typically is from about 50 to 5,000 ppm by weight, preferably 100 to 4,000 ppm by weight, and most preferably about 150 to 3500 ppm by weight. As used herein, the term "monofunctional material" means any process-related material having a single functional group capable of reacting with a glycol monomer under typical polymerization conditions.

Each of the foregoing materials need not be present in the amounts mentioned above if the desired advantage attributable to that material is not required in the desired monomer application.

By way of example, the crude NDA can be reslurried to yield an NDA monomer having the approximate specifications set forth in Table 2, below.

TABLE 2

| Material | Level |
| --- | --- |
| trifunctionals | 5,500 +/− 1,500 ppm |
| monofunctionals | 2,000 +/− 1,000 ppm |
| metals (Co + Mn) | 1000 +/− 500 ppm |
| color bodies | 150 +/− 120 ppm |

Examples 1 and 2, below, demonstrate the effect of cobalt and manganese metal on the rate of polymerization of an aromatic polymer. The effect of catalytic metals in NDA monomer in a purified terephthalic acid (PTA)/ naphthalenedicarboxylic acid (NDA) polymer was demonstrated by comparing the polymerization of an antimony-catalyzed 92 mole percent PTA/8 mole percent NDA mixture polymerized with ethylene glycol (the polymer being hereafter referred to as "PETN-8") with that of a similar mixture that had been "spiked" with 90 ppm by weight of cobalt (as cobalt acetate) and 30 ppm by weight of manganese (as manganese acetate). The polymerization times for both mixtures were measured for pressure esterification, atmospheric esterification and polycondensation reactions.

EXAMPLE 1

In this example, the melt polymerization of PETN-8 without cobalt and manganese concentrations in the range of the invention was demonstrated. The following materials were placed into a 56-liter, helical-agitated reactor: 12.86 kg of ethylene glycol, 27.53 kg of terephthalic acid, 3.12 kg of 2,6-naphthalene dicarboxylic acid, 1.34 grams of tetramethylammonium hydroxide, 8.46 grams of antimony trioxide, and 3.00 grams of cobalt acetate (20 ppm based on polymer yield). The initial reactor temperature was 107° C. and the reactor was pressurized with 40 psig nitrogen pressure. The melt temperature was increased to 223–246° C. and water was removed while the pressure was maintained at 40 psig. When water evolution stopped, the pressure was reduced to atmospheric and pressure esterification was completed. The pressure esterification time was 218 minutes.

The melt temperature then was increased to 263° C. and atmospheric esterification was continued for 60 minutes. An additional 100 grams of ethylene glycol and 3.83 grams of phosphoric acid were added. The reactor pressure was decreased from atmospheric to 3 mm Hg over a period of 65 minutes as the melt temperature was increased to 285° C. Melt polycondensation was continued for an additional 108 minutes for a total of 173 minutes of polycondensation time to reach an agitator torque value of 1800 pound-inches. The product was stranded, quenched, and pelletized. The product had an inherent viscosity of 0.58 dL/g measured in 60/40 phenol/tetrachloroethane at 30° C. and a concentration of 0.4 g/dL.

EXAMPLE 2

The following example demonstrates the melt polymerization of PETN-8 with cobalt and manganese concentrations present in the range of the invention. Example 1 was repeated with the same raw materials and weights except that 4.42 grams (28 ppm based on polyester weight) of manganese acetate was added and the amount of cobalt acetate added was 13.59 grams (91 ppm based on polyester weight). Using identical temperatures and pressures, the pressure esterification time was 220 minutes. The atmospheric esterification time was 60 minutes and the polycondensation time at the 285° C. melt temperature required to obtain 1800 pound-inches of torque was 117 minutes. The product's inherent viscosity was 0.59 dL/g.

As can be seen by comparing Examples 1 and 2, the pressure and atmospheric pressure esterification reactions were completed in about 220 and 60 minutes respectively for both the "spiked" and control samples of Examples 1 and 2. Beneficially, however, the polycondensation reaction of the "spiked" sample was completed in about 117 minutes, as compared to about 173 minutes for the control sample. The substantial reduction in reaction time is believed to provide a major economic advantage in use.

Example 3, below, demonstrates that the presence of mono- and tricarboxylic acid impurities does not adversely effect the melt polymerization of PETN-8.

EXAMPLE 3

Example 1 was repeated with the same raw materials and weights as the control except that 12.57 grams of trimellitic acid, 3.80 grams of 2-formyl-6-naphthoic acid, 2.22 grams of 2-naphthoic acid, and 0.19 grams of 2-methyl-6-naphthoic acid were added. High purity NDA obtained by the hydrolysis of NDC was used in the control, while reslurried crude NDA obtained directly from an oxidation of DMN was used in the sample in accordance with the invention. The composition and characteristics of the control and the mono- and trifunctional-containing sample are set forth below. Color bodies were present in the crude sample but were not quantified.

|  | Control | Invention |
|---|---|---|
| Impurity (ppm) | | |
| Tricarboxylic Acids | None | 4,029 |
| Monocarboxylic Acids | 109 | 1,993 |
| Catalyst Level (ppm) | | |
| Cobalt | 20 | 90 |

-continued

|  | Control | Invention |
|---|---|---|
| Manganese | None | 30 |
| Antimony | 200 | 200 |
| Process Time (Minutes) | | |
| Pressure Esterification | 218 | 215 |
| Atmospheric Esterification | 60 | 60 |
| Polycondensation | 173 | 118 |
| Polyester Properties | | |
| Inherent Viscosity, dL/g | 0.58 | 0.56 |
| Color, *b value | 0.38 | +14.62 |

The reduction in polycondensation time from 173 minutes to 118 minutes in accordance with the present invention is believed to be of major economic significance.

With respect to color, it should be noted that the *b color value noted above is a tristimulous color value on the blue/yellow scale. On this scale, a negative value appears blue and a positive value appears yellow, but with *b values greater than about +10, the visual appearance is brown. Therefore, the polyester prepared according to the invention particularly was suitable for beer bottle and other brown container applications without the added cost and environmental concern of the addition of an organic dye or pigment. Such color body-containing polyesters of this invention also are useful as relatively low cost polyesters in applications where white color is not a requirement, such as for industrial fibers and insulating films.

Example 4, below, illustrates the increased ability of polymers in accordance with the invention to polymerize in the solid state.

EXAMPLE 4

3.0 gram polymer pellets produced from the materials of Examples 1 and 2 were crystallized in an oven at 150° C. for 2.0 hours. The pellets were placed in test tubes, vacuum was applied, and the test tubes placed in an oil bath at room temperature. The oil was heated over a period of 200 minutes to 410° F. which was considered the starting point for solid state polymerization. Samples were periodically removed from the oil bath and the following data obtained:

|  | Inherent Viscosity (dL/g) | |
|---|---|---|
| Time (Hours) | Control | Invention |
| Start | 0.60 | 0.55 |
| 1.0 | 0.61 | 0.62 |
| 2.0 | 0.62 | 0.64 |
| 4.0 | 0.65 | 0.68 |
| 6.0 | 0.71 | 0.73 |
| 8.0 | 0.75 | 0.77 |
| Rate (dL/g) | 0.0188 | 0.0238 |

The foregoing data demonstrates an approximately 40 percent solid state polymerization rate increase for the invention compared to the control.

Examples 5 and 6, below, demonstrate that films can be formed and stretched from polymers in accordance with the invention, and that the presence of extraneous material in the polymer does not adversely affect the film product.

EXAMPLE 5

Solid state polymerized pellets in accordance with the invention from Example 4 were dried for 16 hours at 150°

C. and melt extruded using a Killion Model KL-125 single screw extruder equipped with a 1.25 inch screw with a length to diameter ratio of 24 to 1 (L/D=24/1). The extruder was equipped with a six inch adjustable lip sheet die and three chilled temperature rolls for take-off. A heater temperature profile of 515/525/530/530/530/500° F. (feed throat to die) was employed and the screw speed was 75 rpm. High quality, amorphous sheet having a thickness of approximately 23 mils was produced.

EXAMPLE 6

Samples of the sheet from Example 6 were biaxially oriented in a T. M. Long stretcher. The samples were heated to 226–244° F. for a period of 2.0 minutes and stretched at a stain rate of approximately 300%/second to produce 3×3 biaxially oriented films.

The following film properties were measured:

| Property | Control | Invention |
| --- | --- | --- |
| Crystallinity, % | 25.0 | 23.7 |
| Carbon Dioxide Permeation (cc-mil/100 in 2-day-atm @ 35° C.) | 34.2 | 31.2 |

As can be seen from the foregoing data, the PETN-8 copolyester sample of the invention which contained high levels of moncarboxylic acids and tricarboxylic acids exhibited essentially the same level of crystallinity as the control sample and both films had similar carbon dioxide permeation values. However, the lower permeation value for the invention translates into longer shelf-life for packaging applications. Both films were very tough and showed no evidence of brittleness.

Other preferred polyesters which can employ NDA monomer product in accordance with the present invention include any PTA/NDA polymer having molar ratios of PTA to NDA of 99:1 to 0:100. Preferred ranges of NDA to PTA in NDA/PTA polyesters will range from 2 to 15 mole percent NDA to 98 to 85 mole percent PTA, with 2 to 9 mole percent NDA to 98 to 91 mole percent PTA being more preferred. NDAs useful in the invention can be any polymerizable isomer such as 2,6-, 1,5-,1,4- and 2,7-NDA, as well as mixtures thereof. The polyesters also can include up to about 15 mole percent of other carboxylic acids such as isophthalic acid and/or adipic acid. The polyester also may incorporate up to about ten mole percent of a glycol such as diethylene glycol, 1,4-butanediol, polybutadiene glycol or 1,4-cyclohexanedimethanol, or mixtures thereof. With respect to the ranges of process-related materials set forth in Table 1, above, it should be noted that higher levels of monomer impurities a re preferred in monomer product intended to be used as small fractions of a copolymer, while lower levels of impurities will be preferred where the monomer product comprises large fractions of a copolymer or where the end product is a homopolymer.

The inherent viscosity of polyesters in accordance with the present invention as measured in a 60/40 solution of phenol/tetrachloroethane at 30° C. and a concentration of 0.4 grams/dL typically will be between about 0.40 to 1.00 dL/gram, preferably about 0.50–0.90 dL/g, and most preferably between about 0.60–0.80 dL/g.

The dicarboxylic acid component of polyesters in accordance with the invention optionally may be modified with up to 15 mole percent of one or more different dicarboxylic acid s other than terephthalic acid and 2,6-naphthalenedicarboxylic acid. Such additional dicarboxylic acids include aromatic dicarboxylic acids preferably having 8 to 14 carbon atoms, aliphatic dicarboxylic acids preferably having 4 to 12 carbon atoms, or cycloaliphatic dicarboxylic acids preferably having 8 to 12 carbon atoms. Examples of dicarboxylic acids to be included are phthalic acid, isophthalic acid, cyclohexanediacetic acid, 4,4'-biphenyldicarboxylic acid, succinic acid, glutaric acid, adipic acid, fumaric acid, azelaic acid, sebacic acid, 1,4-cyclohexanedicarboxylic acid, resorcinoldiacetic acid, diglycolic acid, 4,4-oxybis(benzoic) acid, 1,12-dodecanedicarboxylic acid, 4,4'-sulfonyldibenzoic acid, 4,4'-methylenedibenzoic acid, trans 4,4'stilbenedicarboxylic acid, 2,6-dicarboxytetralin, 2,6-dicarboxydecalin, and the like.

Other additives and stabilizers known in the art such as glass fibers, mineral reinforcement, oxygen scavengers, diethylene glycol suppressants, optical brightening agents and phosphorous-containing stabilizers can be incorporated into monomer product or polymers made therefrom in accordance with the invention.

Monomers in accordance with the invention also may be used to produce homopolymers and copolymers from relatively pure acids by adding the materials described herein in the amounts set forth herein.

For example, metal salts particularly useful for preparing metal-containing monomers include cobalt and manganese alkylates such as acetates, halides, especially bromides, and organic acid salts, particularly aromatic salts. When adding salts to relatively pure aromatic acids, metal concentrations can range from about 20 to 10,000 ppm by weight, more preferably between about 50 to 2000 ppm by weight, and most preferably between about 100–1000 ppm by weight.

If Co and Mn are added to produce a monomer in accordance with the invention, the molar ratio of Co to Mn can range from 5:1 to 0.2:1, with the preferred ratios being between 4:1 to 0.25:1, and the most preferred ratios being between 3:1 and 0.5:1.

Polymers in accordance with the invention can be produced in the same manner as polymers are produced from purer monomers of the same acids. Such polymerization reactions are well-known in the art. See, for example, *The Encyclopedia of Chemical Technology*, Vol. 18, pp. 531–594, John Wiley and Sons (1982), the disclosure of which is hereby incorporated by reference.

Co- and homopolyesters produced in accordance with the invention can be used to manufacture sheets and biaxially oriented films, fibers, stretch blow molded containers and any other application where such polyesters typically are employed. See, for example, *Plastics Engineering Handbook*, 4th Edition, Van Nostrand Reinhold Company (1976), the disclosure of which is hereby incorporated by reference.

The presence of metals, color bodies and other impurities in the acid monomer of the present invention make these monomers particularly useful in NDA-copolymer applications where the presence of color is desired or not objectionable, as well as where enhanced high temperature performance is required. Typical applications particularly suitable for use of copolymers in accordance with the invention are containers for food or beverages that require heating or pasteurization and which must exhibit dimensional stability during and after the heating or pasteurization process. This is especially true where the packaged material contains carbon dioxide or another gas which will generate substantial internal package pressure when heated. Specific examples of such applications are pasteurizable bottles for beer, and bottles for fruit juices such as prune juice, where package heatability and color are desired package characteristics. The utility of NDA/PTA copolymers is demonstrated by Example 7 below.

EXAMPLE 7

One half liter capacity, long neck, pasteurizable amber beer bottles having a champagne base were fabricated from experimental copolymers containing reslurried acid monomer in accordance with the composition described in Table 2, above.

In Example 7A, the PETN-3 copolymer employed contained 3 mole percent of the reslurried NDA and 97 mole percent of a purified terephthalic. In this Example, a 35.0 gram injection molding preform was prepared. The preform contained approximately 15 grams of copolymer in the shoulder area, about 10 grams of copolymer in the panel area, and about 10 grams of material in the base area.

In Example 7B, a PETN-5 copolymer contained 5 mole percent of the reslurried NDA and 95 mole percent of the same purified terephthalic acid. In this Example, a 34.1 gram injection molding preform was prepared. The preform contained approximately 14.7 grams of copolymer in the shoulder area, about 10 grams of copolymer in the panel area, and about 9.4 grams of material in the base area.

The preforms of Examples 7A and 7B were blown into 0.5 liter bottles using a Sidel SBL2/3 stretch blow molding machine. Carbonated water containing about 2.9 to 3.1 volumes of carbon dioxide was added to each bottle to a predetermined fill line and capped.

The capped bottles were placed in a pasteurization chamber and sprayed with 71 degree Centigrade water until the bottle contents reached a temperature of about 63° C. The spray water temperature was then reduced to 64° C. to maintain the bottle contents at 63° C. for an additional 15 minutes. Spray water temperature was then reduced until the bottle contents reached 40° C., after which time the bottles were chilled to room temperature in a cold water bath.

Several physical parameters of the pasteurized bottles were measured to determine the effects on the bottles from the pasteurization process. The results of those measurements are summarized in Table 3 below.

TABLE 3

| Bottle material | PETN-3 | PETN-5 |
|---|---|---|
| Resin IV | 0.80 | 0.80 |
| Dimensional Changes (% increase) | | |
| Height | 0.43 | 0.26 |
| Diameter | | |
| Upper Bumper | 1.94 | 2.15 |
| Mid Panel | 1.74 | 0.48 |
| Lower Bumper | 1.03 | 1.04 |
| Neck | 1.27 | 1.36 |
| Fill Line Drop (in.) | 0.60 | 0.69 |
| Perpendicularity (in. off bottle center line) | 0.119 | 0.152 |
| Pressure (volumes) | 2.71 | 2.68 |

In the case of Examples 7A and 7B, both bottles' dimensional changes were judged acceptable based on pressure retention (at least 75% of the prepasteurization pressure was retained when initially charged to a pressure of about 3 volumes), and perpendicularity (deviation from the vertical less than 0.25 inches for the vertical radial axis of bottle symetry when the pasteurized bottle is standing on its base, with the deviation measured at the top of the bottle. Fill line drops of less than 3 percent also are preferred.

It was also found that injection blow molding bottle preforms containing between about 40–46 weight percent of their material in the shoulder region, 26–32 weight percent of their material in their panel region and 25–31 weight percent of their material in the base region were most successful in withstanding the pasteurization tests. These approximate preform weight distributions and geometries are believed to be useful for half liter bottles formed from other polymers and are believed to be scalable for producing pasteurizable bottles of other volumes.

While the foregoing examples describe the invention with respect to certain naphthalenic acid monomer products, those of ordinary skill in the art will recognize that the invention is equally useful in connection with monomers such as terephthalic acid, isophthalic acid and the like, with process-related materials present in approximately the same ranges when corrected for the molecular weight difference between naphthalenic and other aromatic monomers. Additionally, when monomers according to the present invention are used to make copolymers, the process-related materials present in accordance with the present invention may be present, for example, in any one monomer, or in more than one monomer. For these reasons, our invention is intended to be limited only by the scope of the following claims.

We claim:

1. A process for producing a naphthalenic dicarboxylic acid monomer product suitable for the manufacture of polyesters, said process comprising the steps of:
   oxidizing a naphthalenic feedstock to produce a crude naphthalenic dicarboxylic acid;
   processing the crude naphthalenic dicarboxylic acid to produce a naphthalenic dicarboxylic acid monomer product comprising at least 90 mole percent of the acid monomer and one or more process-related materials selected from the group consisting of between 50 and 5,000 ppm of monofunctional materials, between 50 and 10,000 ppm of trifunctional materials, between 50 and 500 ppm of color bodies, and between 50 and 10,000 ppm of metals;
   wherein the processing step includes slurrying the crude naphthalenic dicarboxylic acid in a solvent selected from the group consisting of water, aliphatic organic acids having between 2 and 4 carbon atoms, and mixtures thereof.

2. The process of claim 1 wherein the processing step includes slurrying the crude naphthalenic dicarboxylic acid in a solvent selected from the, group consisting of water, aliphatic organic acids having between 2 and 4 carbon atoms, and mixtures thereof.

3. The process of claim 2 wherein the slurrying step is performed at a temperature of about 60 to 125° C., at a pressure of from about 0.5 to 3 atmospheres, and at a solvent to crude naphthalenic acid weight ratio of about 0.5:1 to 20:1.

4. The process of claim 2 wherein the slurrying step is performed at a temperature of about 75 to 110° C., at a pressure of from about 1 to 2 atmospheres, wherein the solvent comprises at least 50 mole percent acetic acid, and at a solvent to crude naphthalenic acid weight ratio of about 1:1 to 10:1.

5. The process of claim 1 further comprising the step of producing a homopolymer or copolymer article from monomers comprising the naphthalenic dicarboxylic acid monomer product, said article being selected from the group consisting of sheets, films, oriented films, fibers, injection molded articles, and blow molded articles.

6. The process of claim 1 wherein the copolymer is formed from monomers comprising between about 2 and 15 mole percent of the naphthalenic dicarboxylic acid monomer product and from between about 98 and 85 mole percent of one or more aromatic acids selected from the group consisting of terephthalic acid, isophthalic acid, and adipic acid, and mixtures thereof.

7. The process of claim 1 wherein the copolymer is formed from monomers comprising between about 2 and 9 mole percent of the naphthalenic dicarboxylic acid monomer product and from between about 91 and 98 mole percent of terephthalic acid.

8. A polyester comprising at least 2 mole percent of a naphthalenic dicarboxylic acid monomer product having between about 50 to 250 ppm of color bodies and a tristimulus color value of greater than +10 on a yellow/blue scale wherein said naphthalenic dicarboxylic acid monomer product is produced by the process of:

oxidizing a naphthalenic feedstock to produce a crude naphthalenic dicarboxylic acid;
  processing the crude naphthalenic dicarboxylic acid to produce a naphthalenic dicarboxylic acid monomer product comprising at least 90 mole percent of the acid monomer and one or more process-related materials selected from the group consisting of between 50 and 5,000 ppm of monofunctional materials, between 50 and 10,000 ppm of trifunctional materials, between 50 and 500 ppm of color bodies, and between 50 and 10,000 ppm of metals.

9. A copolymer formed from monomers comprising between about 2 and 10 mole percent of a polymerized naphthalenic dicarboxylic acid monomer product and from between about 98 and 91 mole percent of terephthalic acid wherein;

said polymerized naphthalenic dicarboxylic acid monomer product comprises at least 90 mole percent of the acid monomer and one or more materials selected from the group consisting of between 50 and 5,000 ppm of monofunctional materials, between 50 and 10,000 ppm of trifunctional materials, between 50 and 500 ppm of color bodies, and between 50 and 10,000 ppm of metals, and combinations thereof.

10. An article formed from the copolymer of claim 9, said article being selected from the group consisting of sheets, films, oriented films, fibers, injection molded articles, and blow molded articles.

11. A process comprising:

(a) producing a naphthalenic dicarboxylic acid monomer product by oxidizing a naphthalenic feedstock to produce a crude napthalenic dicarboxylic acid comprising a naphthalenic dicarboxylic acid useful as a monomer in a polymerization reaction and process-related materials formed during the manufacture of the crude naphthalenic dicarboxylic acid; slurrying the crude naphthalenic dicarboxylic acid in a solvent to remove a portion of process-related materials from the crude naphthalenic dicarboxylic acid; recovering solid monomer from the slurry to produce a naphthalenic dicarboxylic acid monomer product comprising at least 93 mole percent of the acid monomer and one or more process-related materials selected from the group consisting of between 50 and 5,000 ppm of monofunctional materials, between 50 and 10,000 ppm of trifunctional materials, between 50 and 500 ppm of color bodies, and between 50 and 10,000 ppm of metals;

(b) polymerizing the naphthalenic dicarboxylic acid monomer product into a homopolymer or a copolymer without first performing an intervening process step intended to remove the process-related materials from the monomer product prior to conducting the polymerization.

12. The process of claim 11 wherein the copolymer is formed from monomer comprising between about 2 and 9 mole percent of the polymerized naphthalenic dicarboxylic acid monomer product and from between about 98 and 91 mole percent of terephthalic acid.

13. The process of forming, from the copolymer of claim 12, an article selected from the group consisting of sheets, films, oriented films, fibers, injection molded articles, and blow molded articles.

14. A pasteurizable blow-molded bottle prepared from a polymerized material comprising a copolymer formed by the process of claim 12, wherein the copolymer contains between about 2 and 9 mole percent of the naphthalenic dicarboxylic acid monomer product and from between about 98 and 90 mole percent of terephthalic acid, said bottle being capable of containing a gas-containing liquid during a pasteurization process in which the temperature of the gas-containing liquid is maintained at a temperature of at least 60° C. for at least 15 minutes during said process, and wherein said bottle is capable of retaining at least 70 percent of an initial gas pressure when charged to an initial gas pressure of about 3 volumes of gas per bottle volume.

15. The bottle of claim 14, wherein, after pasteurization, the bottle has a vertical axis of radial symetry through the bottle which deviates from perpendicular of less than 0.25 inches.

16. The bottle of claim 14, wherein the bottle is a bottle having an approximate 500 milliliter capacity, and wherein the bottle is blown from a preform having a shoulder area, a panel area and a base area, said areas expanding during the blowing process under exposure to heat and pressure to form a blow molded bottle, and in which the shoulder area contains between about 14 to 16 grams of polymer, wherein the panel area contains between about 9 to 11 grams of polymer, and wherein the the base contains between about 8.5 and 11 grams of polymer.

* * * * *